US009661988B2

(12) United States Patent
Dahmen et al.

(10) Patent No.: US 9,661,988 B2
(45) Date of Patent: May 30, 2017

(54) OPTICS TUBE FOR AN ENDOSCOPE, ENDOSCOPE, AND METHOD FOR MOUNTING AT LEAST ONE ROD LENS IN AN OPTICS TUBE

(71) Applicant: Karl Storz GmbH & Co. KG, Tuttlingen (DE)

(72) Inventors: Jan Dahmen, Tuttlingen (DE); Walter Vogel, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 302 days.

(21) Appl. No.: 14/185,512

(22) Filed: Feb. 20, 2014

(65) Prior Publication Data

US 2014/0235947 A1   Aug. 21, 2014

(30) Foreign Application Priority Data

Feb. 20, 2013   (DE) .......................... 10 2013 101 650

(51) Int. Cl.
| | | |
|---|---|---|
| *A61B 1/04* | (2006.01) | |
| *A61B 1/00* | (2006.01) | |
| *A61B 1/002* | (2006.01) | |
| *G02B 23/24* | (2006.01) | |
| *B29C 65/00* | (2006.01) | |

(52) U.S. Cl.
CPC .......... *A61B 1/00142* (2013.01); *A61B 1/002* (2013.01); *A61B 1/0011* (2013.01); *A61B 1/00096* (2013.01); *G02B 23/2476* (2013.01)

(58) Field of Classification Search
CPC ............ A61B 1/00142; A61B 1/00096; A61B 1/0011; A61B 1/002; A61B 1/055; G02B 23/2476
USPC ...... 600/114, 128, 129, 138; 156/272.4, 293
See application file for complete search history.

(56) References Cited

U.S. PATENT DOCUMENTS

| | | | | |
|---|---|---|---|---|
| 5,836,897 A | * | 11/1998 | Sakurai ............ | A61B 17/22012 601/2 |
| 6,146,326 A | * | 11/2000 | Pollack .................. | A61B 1/002 600/133 |
| 6,471,640 B1 | * | 10/2002 | Frische .................. | A61B 1/002 359/434 |
| 7,708,689 B2 | * | 5/2010 | Deppmeier .............. | A61B 1/04 600/138 |

FOREIGN PATENT DOCUMENTS

| | | |
|---|---|---|
| DE | 3431631 A1 | 3/1986 |
| DE | 19750685 A1 | 6/1999 |
| DE | 102006041920 A1 | 3/2008 |
| EP | 1776918 A2 | 4/2007 |
| EP | 2283768 A1 | 2/2011 |
| WO | 9905959 A1 | 2/1999 |

* cited by examiner

*Primary Examiner* — Timothy J Neal
(74) *Attorney, Agent, or Firm* — Whitmyer IP Group LLC

(57) ABSTRACT

In an optics tube for an endoscope, a lens arrangement including at least one rod lens is received in the inside of the optics tube, wherein a sleeve is fixed on the at least one rod lens and at least partially encloses the rod lens, and wherein the sleeve is welded to the optics tube. The invention also relates to an endoscope having such an optics tube, and to a method for mounting at least one rod lens in the inside of an optics tube.

14 Claims, 5 Drawing Sheets

OPTICS TUBE FOR AN ENDOSCOPE, ENDOSCOPE, AND METHOD FOR MOUNTING AT LEAST ONE ROD LENS IN AN OPTICS TUBE

FIELD OF THE INVENTION

The present invention relates to an optics tube for an endoscope, to an endoscope having such an optics tube, and to a method for mounting at least one rod lens in an optics tube.

BACKGROUND OF THE INVENTION

Endoscopes are used to view cavities in the human or animal body and also in technical objects. An endoscope typically comprises an elongate endoscope shaft, which is suitable for insertion into the cavity to be viewed, and a head that can have attachments and control elements and also an eyepiece lens. Inside the endoscope shaft and the head there is an optical system for transmitting an endoscopic image from the distal end of the endoscope, i.e. the end remote from the observer, to the proximal end, i.e. the end near the observer. For this purpose, the optical system comprises in particular a distally arranged objective for receiving the endoscopic image, an image carrier, and an eyepiece arranged at the proximal end of the endoscope, with an eyepiece lens for viewing the transmitted endoscopic image. The endoscope can be designed in particular as a rigid endoscope with a rigid endoscope shaft and can have, as its image carrier, an arrangement of rod lenses accommodated in an optics tube arranged inside the endoscope. Moreover, the endoscope can have an illuminating device for illuminating the cavity to be viewed, and, if appropriate, it can have further devices, such as channels for endoscopic work instruments.

To assemble the optical components in the optics tube of a rigid endoscope, they are usually pushed into the optics tube from the proximal end and in the sequence and arrangement predefined by the lens design. In particular, the objective, one or more rod lenses and one or more aperture stops or spacers are pushed in succession into the optics tube. For this purpose, the optical components have an external diameter that is slightly smaller than the internal diameter of the optics tube. With the aid of a system spring and a system closure guide, the entire optical system is pretensioned in the distal direction and thereby pretensioned against a distal closure piece of the optics tube, which can be provided in particular by a cover glass. In this way, the optical elements are held in the longitudinal direction in the respective position that has been predetermined on the basis of the lens design.

During their use, endoscopes are exposed to considerable mechanical and thermal stresses. Thus, during their handling, the endoscope can be subjected to accelerations and vibrations or jolts, or the endoscope shaft may be bent if handled without due care. Accelerations and in particular vibrations can lead to movements of the lenses and of the other optical components relative to one another and relative to the optics tube, possibly resulting in abrasion, which leads to the development of stray light. Moreover, the optical elements may tilt relative to one another and/or move axially out of place relative to one another, which can likewise impair the quality of the endoscopic image conveyed. Vibrations and bending of the endoscope shaft can cause the lenses to bulge or even break, the rod lenses being particularly at risk on account of their length. Moreover, medical endoscopes are exposed to hot steam and high pressure when sterilized by autoclaving, in which case leaks in the seal of the optical system can likewise lead to an impairment of the endoscopic image. Considerable costs can thus arise in the production and in the use of an endoscope.

In order to fix the rod lenses safely and in the correct position in the inside of the optics tube, and to avoid bending of the endoscope shaft being transferred to the rod lenses, it is known from the laid-open application DE 19750685 A1 that the rod lenses are positioned at a defined radial distance from the inside face of the optics tube by means of at least two centering aids, and that an elastic adhesive connection is produced between the outside of the rod lens and the inside face of the tube at at least two locations spaced axially apart from each other. Each centering aid has centering elements distributed uniformly about the circumference of the rod lens.

SUMMARY OF THE INVENTION

It is an object of the present invention to make available an optics tube of the stated type for an endoscope, an endoscope having such an optics tube, and a method for mounting at least one rod lens in an optics tube, the aim being to permit secure positioning and fixing of the optical components in a simple manner which reduces as far as possible the number of necessary components and the manufacturing cost of the necessary components.

This object is achieved by an optics tube, by an endoscope, and by a method according to the independent claims.

Further developments of the invention are set forth in the dependent claims.

An optics tube according to the invention for an endoscope is preferably elongate and has, on its inside, a lens arrangement comprising at least one rod lens. The rod lens can be in one piece or can be composed of a plurality of lenses cemented together. In the present application, the term "rod lens" also includes a flat rod. The lens arrangement comprises in particular one or more relay lens systems by means of which an endoscopic image received from an objective arranged at the distal end of the endoscope is transmitted to the proximal end of the endoscope. The objective, or a portion of the objective, and if appropriate a portion of the eyepiece can also be accommodated in the optics tube.

According to the invention, a weldable sleeve is fixed on the at least one rod lens and at least partially encloses the rod lens. The rod lens is in particular cylindrically off-centered and fixes the weldable sleeve on the jacket surface of the rod lens, coaxially with respect to the longitudinal axis of the rod lens. The weldable sleeve of the at least one rod lens is welded to the optics tube in order to fix the rod lens to the latter. For this purpose, the sleeve has an external diameter that is slightly smaller than or at least the same as the internal diameter of the optics tube, such that the rod lens can be inserted with the weldable sleeve into the optics tube. The sleeve and the optics tube are also preferably each cylindrical.

The fact that a sleeve is fixed on the at least one rod lens and at least partially encloses the rod lens, and that the sleeve is welded to the optics tube, permits a secure fixing of the rod lens at a desired position inside the optics tube, with only a small number of components being needed for this. Therefore, even in the event of vibrations, a displacement or tilting of the rod lenses cannot take place, such that it is possible to avoid the development of wear and a deterioration of the image quality. Moreover, this allows the rod lens to be fixed inside the optics tube without adversely affecting the sealing of the optics tube for leaktight sealing of the optical system accommodated in the optics tube.

The optics tube and the sleeve are preferably metallic, in particular preferably made from the same metallic material. This makes it easier to weld the sleeve to the optics tube.

Advantageously, the sleeve is adhesively bonded or cemented to the rod lens. For this purpose, the sleeve can have an internal diameter that is slightly smaller than an external diameter of the rod lens, such that an adhesion gap remains between the outside of the rod lens and the inside face of the sleeve when the latter is pushed over the rod lens, which adhesive gap is filled at least partially with adhesive for fixing the sleeve on the rod lens. The sleeve can thus be fixed on the rod lens in a simple and safe way.

It is also particularly advantageous that the sleeve encloses the at least one rod lens along a guide length which is only a part of the overall length of the rod lens. Preferably, the guide length is at most 50% of the length of the rod lens, particularly preferably at most one third of the length or one quarter of the length of the rod lens. Thus, only a suitably short portion of the rod lens is enclosed by the sleeve welded to the optics tube. This affords the further advantage that a bending of the optics tube is transferred only to a small extent to the rod lens, namely in the area of the guide length, in which area the rod lens is additionally supported by the sleeve. In the other portions, the wall thickness of the sleeve means that the rod lens does not touch the inside face of the optics tube, such that a bending of the optics tube cannot transfer to the rod lens and, even in the event of vibrations, the rod lens does not come into contact with the optics tube. In this way, it is possible to prevent damage to the rod lens by bulging or by the lens breaking.

According to a preferred embodiment of the invention, the sleeve is fixed approximately centrally on the rod lens. In this embodiment, the proximal and distal ends of the rod lens protrude beyond the sleeve and beyond the guide length defined by the latter and, in the portions protruding beyond the sleeve, they maintain a distance from the inside wall of the optics tube according to the wall thickness of the sleeve. The rod lens can be securely fixed in this way, and it is possible to avoid the optics tube being touched by the rod lens outside the relatively short guide length of the sleeve.

According to another preferred embodiment of the invention, the lens arrangement received in the optics tube comprises at least one further rod lens which is adjacent to the at least one rod lens, i.e. follows or precedes the latter in the light path. The sleeve encloses the mutually facing end portions of the two adjacent rod lenses and is fixed thereon, particularly by adhesive bonding. The sleeve thus encloses the two rod lenses only partially, such that the rod lenses in the other portions are not enclosed by the sleeve and are spaced apart from the inside wall of the optics tube according to the wall thickness of the sleeve. In this embodiment, the two rod lenses are connected to each other by the sleeve and held at a predetermined distance relative to each other. Therefore, only a single sleeve is needed for the two rod lenses. The unit composed of the two rod lenses and of the sleeve can be inserted as one into the optics tube. This further simplifies the assembly of the optical system and permits secure fixing of the two adjacent rod lenses in the optics tube, and it also reduces the danger of the rod lenses being damaged by bending of the optics tube or by vibrations.

It is also advantageous that a diaphragm is arranged between the two adjacent rod lenses fixed by a sleeve engaging over their end portions. These diaphragms, generally of annular design, serve in particular as aperture stops for limiting the aperture of the transmitted endoscopic image and for reducing coupling-in of stray light. Such a diaphragm can serve at the same time as a spacer, in order to adjust the distance between the mutually facing end surfaces of the rod lenses to a predefined value. Instead of or in addition to the diaphragm, a spacer, for example a spacer sleeve, can be provided. The diaphragm or the spacer can be a separate structural part arranged between the rod lenses over which the sleeve is pushed, or it can also be rigidly connected to the sleeve or be made in one piece with the latter. In this way, a particularly simple embodiment is obtained in which the number of the components to be mounted in the optics tube is further reduced. In particular, the diaphragm can be designed as an aperture stop and can be arranged between two rod lenses which together form a relay lens system, i.e. which effect an inversion for transmitting the endoscopic image. The unit formed by the two rod lenses, by the sleeve and by the aperture stop can thus constitute a complete relay lens system which is pushed singly or multiply, in each case of identical design, into the optics tube. This further facilitates the production and assembly of the endoscope.

Particularly advantageously, the sleeve is made of a ferromagnetic material or has at least one such material. This permits particularly simple handling when positioning the sleeve, and the at least one rod lens fixed thereon, inside the optics tube, since a magnetic force can be applied to the sleeve with the aid of a magnet arranged outside the optics tube.

An endoscope according to the invention has an elongate optics tube which is arranged inside an elongate endoscope shaft and which can also reach into a head of the endoscope. The endoscope shaft is designed as a rigid endoscope shaft, wherein some degree of bending may be admissible. The optics tube can be designed, for example, as an inner tube of an endoscopic lens system, which is here likewise designated as endoscope, or as a system tube of an endoscope, which for example can comprise work channels for endoscopic instruments or further channels. The endoscope, or the endoscopic lens system, also comprises in particular illuminating optics, which typically comprise glass fiber light guides by which the illuminating light generated by an external light source is transmitted to the distal end of the endoscope, from where it radiates in order to illuminate the cavity that s to be viewed.

In a method according to the invention for mounting at least one rod lens in the inside of an optics tube for an endoscope, a first step involves a weldable sleeve being fixed on a rod lens. The sleeve in particular encloses only a portion of the rod lens. The sleeve can also enclose two rod lenses at their respective end portions and can be fixed thereon. In a second step, the one or more rod lenses are pushed with the weldable sleeve into the optics tube, for which purpose the external diameter of the weldable sleeve is slightly smaller than the internal diameter of the optics tube, such that there is sufficient play available for pushing the sleeve into the optics tube. In a third step, the weldable sleeve is welded to the optics tube. The welding can be performed in particular by laser welding, wherein one or more weld points or weld seams can be generated. With the method according to the invention, secure assembly and fixing of the at least one rod lens in the inside of the optics tube is permitted in a particularly simple way. During the assembly of an endoscope, the optics tube, with the lens arrangement accommodated therein, can be pushed into the endoscope shaft and fixed therein.

The sleeve preferably has a ferromagnetic material, is brought to a predefined position by means of a magnetic force applied by a magnet arranged outside the optics tube, and is welded to the optics tube in this position. To ensure that the magnet placed outside the optics tube can apply a suitable magnetic force to the sleeve, the optics tube is preferably made of a non-magnetic material or has a sufficiently thin wall to allow the magnetic force to act through the wall of the optics tube; the optics tube is preferably made of stainless steel. This permits particularly simple positioning of the sleeve and, therefore, of the at least one rod lens connected thereto.

It is also preferable that the weldable sleeve is positioned with the aid of a tubular gauge, which acts as an advancing mandrel, and in so doing is held against an end face of the gauge by a magnetic pulling force applied by the outer magnet. In this way, the sleeve can be brought particularly reliably to a predefined axial position and can be held in this position for the welding operation. In order to hold the sleeve on the end face of the gauge, the outer magnet has in particular an axially symmetrical design and encloses the optics tube.

Particularly advantageously, the sleeve is pressed onto the inside face of the optics tube by a magnet arranged outside the optics tube and is then welded to the optics tube in the position thereby defined. In this way, the play that is needed between the outside of the sleeve and the inside face of the optics tube to permit insertion of the sleeve into the optics tube can be compensated by the sleeve being drawn in a defined manner to one side of the optics tube by the acting magnetic force. An assembly step of this kind is in particular carried out for all the rod lenses of the lens arrangement of the endoscope, such that the optical axes of the rod lenses lie in a common alignment, even if they do not coincide with the center axis of the optics tube. This permits secure fixing of the rod lenses in a common optical axis.

According to another preferred embodiment of the method, the optics tube is placed in a V-shaped groove of an assembly device serving as a bearing and, by means of an external force acting in the direction of the groove, is deformed in such a way that the sleeve bears at one or more circumferentially distributed lines on the inside face of the optics tube. In particular, three axially parallel contact lines arise when the optics tube is pressed into the V-shaped groove. This does not cause tilting or displacement of the rod lens, and the latter therefore remains in its predefined longitudinal position and orientation. In this position, the sleeve is welded at least at one point to the inside face of the optics tube. It is also possible for welding to be done in a weld line which follows a portion of the contact line, preferably the upper contact line lying opposite the V-shaped groove, or with mutually facing or circumferentially distributed weld lines. In this case too, it is advantageous for all the lenses of the lens arrangement of the optics tube to be mounted in this way, such that the optical axes of the lenses are in alignment with one another.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of preferred illustrative embodiments and by reference to the attached drawing, in which.

DETAILED DESCRIPTION OF THE INVENTION

Figure 1:
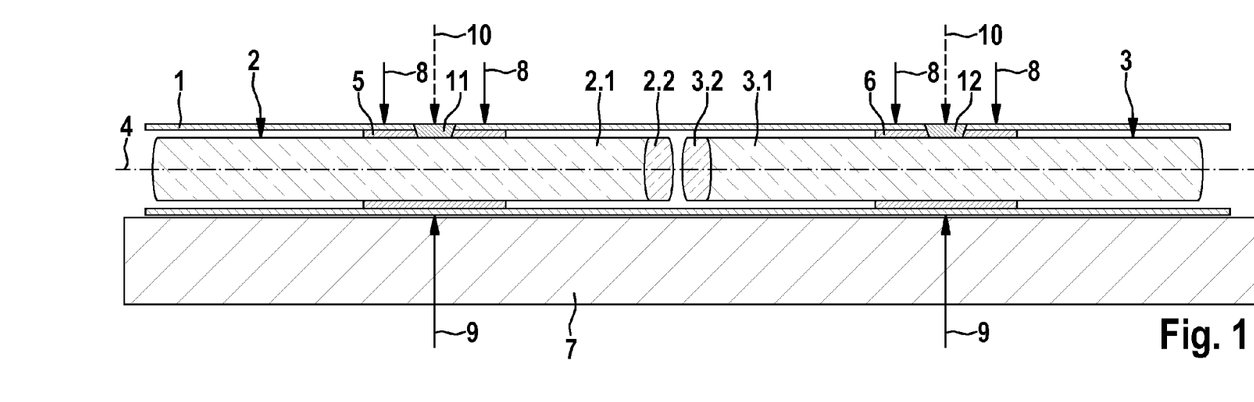
FIG. 1 shows a portion of an optics tube in schematic longitudinal section, with rod lenses received in the inside of the optics tube according to a first illustrative embodiment of the invention, and also an assembly step and an assembly device for a first method according to the invention for mounting the rod lenses in the inside of the optics tube.

As is shown in FIG. 1, in accordance with a first illustrative embodiment of the invention, a plurality of cylindrical rod lenses 2, 3 are arranged in an optics tube 1. The rod lenses 2, 3 each consist of, for example, a convex-concave elongate rod part 2.1, 3.1, which is cemented to a thin lens 2.2, 3.2. In the example shown, the two rod lenses 2, 3, with the thin lenses 2.2, 3.2 arranged facing each other, form a relay lens system by which an intermediate image projected to the left of the left lens surface of the left rod lens 2 by an objective or an upstream relay lens system is imaged to the right of the right lens surface of the right rod lens 3 as a further intermediate image being the inverse of the first one. Depending on the length of the endoscope, the optical system of the endoscope generally comprises a plurality of successive relay lens systems. The rod lenses 2, 3 and the upstream and downstream further relay lens systems or optical elements are arranged in the inside of the optics tube 1 in such a way that their respective optical axes are aligned with one another and form the optical axis 4 of the overall system.

A weldable sleeve 5, 6 is pushed onto the respective rod lenses 2, 3 and is fixed approximately centrally by adhesive bonding. The sleeve 5, 6 is cylindrical with a uniform wall thickness and has a slight underdimension by comparison with the optics tube 1 in order to allow the rod lenses 2, 3 with their respective sleeves 5, 6 to be pushed into the inside of the optics tube 1. In order to prevent a displacement or tilting of the rod lenses 5, 6 and to hold them in a predefined position and orientation, the sleeves 5, 6 are connected to the optics tube 1 by welding. FIG. 1 shows a first variant, as described below, of such a weld connection, and a step in a first assembly method for mounting rod lenses in the inside of the optics tube 1.

According to the first assembly method, after the rod lenses 2, 3 with the sleeves 5, 6 have been pushed to the predefined position inside the optics tube 1, the optics tube 1 is placed in a V-shaped groove of a substantially prismatic assembly device 7 serving as a bearing; this can also be done before the rod lenses 2, 3 are pushed into the optics tube 1. In the perpendicular direction indicated by the arrows 8, pressure is then applied to one side of the optics tube 1 and the latter is thereby slightly deformed, as a result of which the inside face of the optics tube 1 comes into linear contact with the outside of the sleeves 5, 6, and the rod lenses 2, 3 are held axially parallel with the sleeves 5, 6 in the position reached. On account of the opposing force which is exerted by the walls of the V-shaped groove and which is indicated symbolically by the arrows 9 in FIG. 1, one or two further linear contacts between the sleeves 5, 6 and the optics tube 1 form in the lower area. By suitable delivery of heat from outside, for example through the effect of the laser beam 10 of a laser welding installation, the material of the optics tube 1 and of the sleeves 5, 6 is now sufficiently heated to ensure that linear weld seams 11, 12 extending in the longitudinal direction are formed, by which the sleeves 5, 6 are fixedly connected to the optics tube. The weld seams 11, 12 need only take up a part of the length of the contact line between the sleeves 5, 6 and the optics tube 1 and can therefore have a shorter length than the sleeves 5, 6 themselves. The mechanical properties of the optics tube 1 are not appreciably impaired by the weld connection; in particular, the optics tube 1 is not punctured by the welding operation and can therefore be made hermetically tight by means of a suitable seal at the proximal end and at the distal end. By means of the weld connection, the rod lenses 2, 3 are fixed firmly in the inside of the optics tube 1, such that no displacement or tilting of the rod lenses 2, 3 can occur even in the event of vibrations.

After the weld connection has been produced, the application of the lateral force acting in the direction of the arrows 8 is ended, such that the optics tube 1 returns elastically to its original cylindrical shape. Although the underdimensioning of the sleeves 5, 6 means that the rod lenses 2, 3 are not arranged exactly centrally inside the optics tube 1, these rod lenses 2, 3 nevertheless form a common optical axis 4 which, although once again not extending exactly centrally inside the optics tube, is parallel to the longitudinal axis of the optics tube 1. By means of the sleeves 5, 6, the rod lenses 2, 3, in the free portions not enclosed by the sleeves 5, 6, are held at a distance from the optics tube 1, such that in the event of vibrations, and in the event of a certain bending of the optics tube 1, there is no contact between the optics tube 1 and the free areas of the rod lenses 2, 3. In this way, it is possible to reliably avoid damage of the rod lenses.

Figure 2:
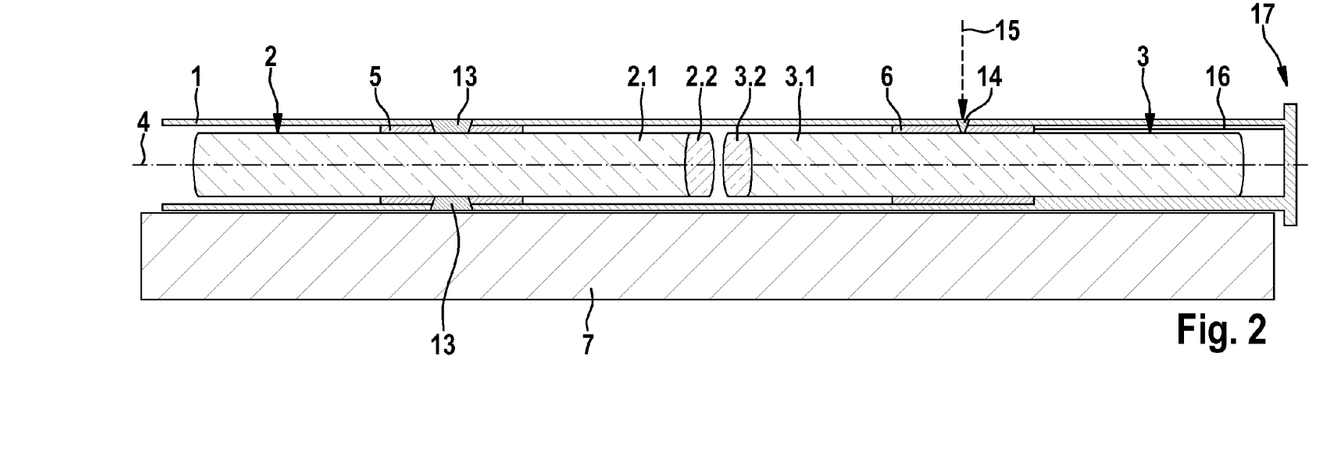
FIG. 2 shows two variants of the optics tube according to FIG. 1, and a gauge for positioning the rod lenses in the longitudinal direction according to the first method.

FIG. 2 shows two further variants of the weld connection between the sleeves 5, 6 and the optics tube 1. The left-hand side of FIG. 2 shows that several weld seams 13 extending in the longitudinal direction of the optics tube 1, and arranged about the circumference of the sleeve 5, can be provided for connection to the optics tube 1, for example two weld seams 13 lying opposite each other, or three weld seams at the aforementioned contact lines between the sleeve 5 and the optics tube 1 during the deformation by the force acting from above. As is shown on the right-hand side of FIG. 2, it is possible that, instead of a linear weld seam, a weld point 14 is also sufficient to fixedly connect the sleeve 6 to the optics tube 1, which weld point can likewise be generated by the action of a laser beam 15 indicated in FIG. 2. Moreover, according to further variants of the weld connection, it is possible to generate one or more short weld seams extending in the transverse direction or, particularly in the case where the underdimensioning of the sleeve 5, 6 with respect to the inner dimension of the optics tube 1 is very slight and no deformation of the optics tube is necessary, it is possible to generate an annularly extending weld seam (not shown in FIGS. 1 and 2). It will be appreciated that preferably both rod lenses 2, 3 of the relay lens system shown in FIGS. 1 and 2, in particular all relay lens systems of the endoscope, can be fixed in the optics tube 1 with weld connections formed according to the same variant.

Figure 3:
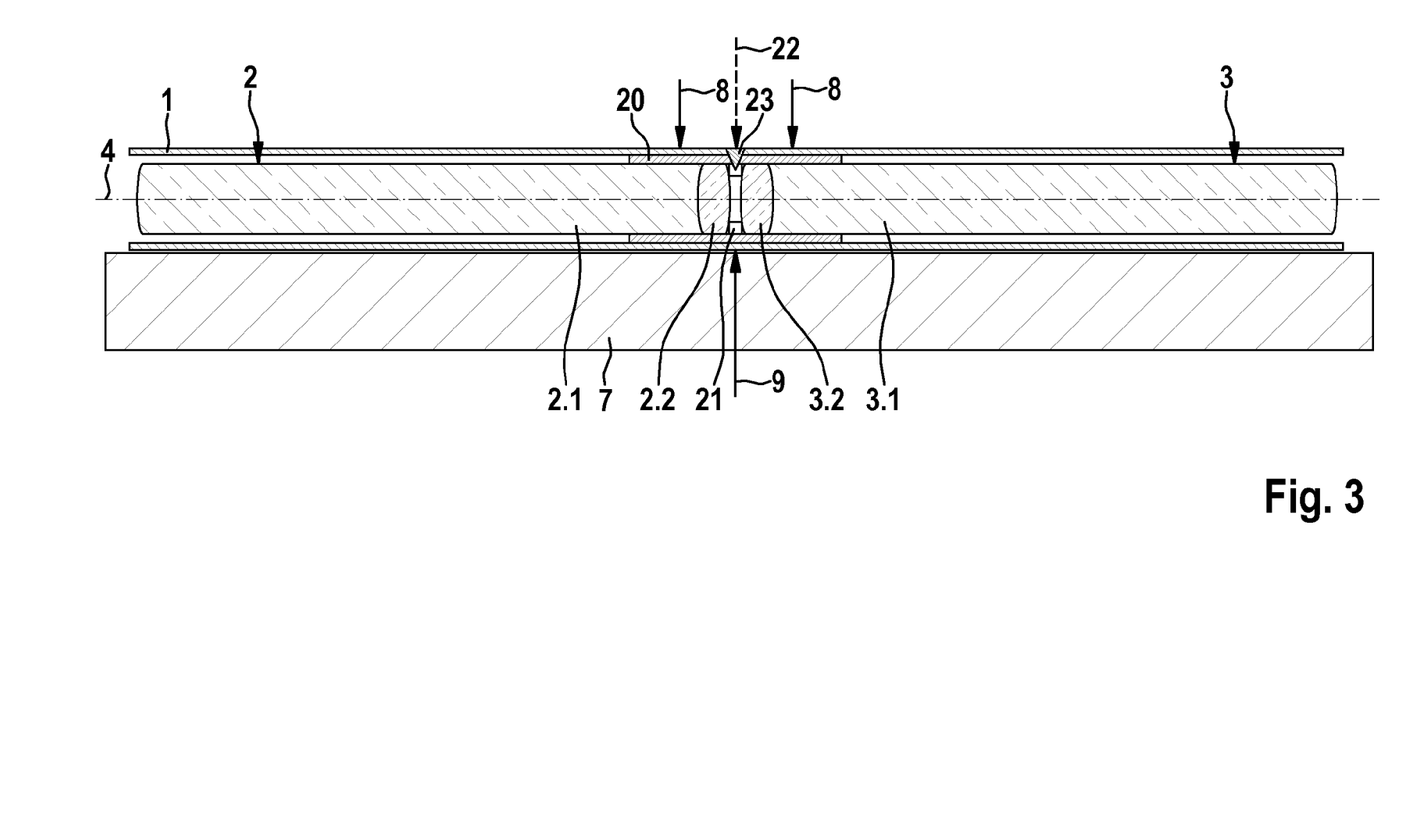
FIG. 3 shows a portion of an optics tube in schematic longitudinal section, with rod lenses received in the inside of the optics tube according to a second illustrative embodiment of the invention.

FIG. 3 shows a portion of an optics tube in longitudinal section, with rod lenses 2, 3 arranged therein according to a second illustrative embodiment of the invention. Here, a sleeve 20 engages around the mutually facing end portions of the two rod lenses 2, 3 of a relay lens system. Arranged between the rod lenses 2, 3 is an annular aperture stop 21, which at the same time serves as a spacer between the two rod lenses 2, 3. The sleeve 20 is fixed by adhesive bonding to the respective end portions of the rod lenses 2, 3. By pushing the rod lenses 2, 3 into the sleeve 20 and adhesively bonding the rod lenses to the sleeve 20, a unit is thereby created which can be pushed as one into the optics tube 1. Otherwise, the embodiment shown in FIG. 3 is designed like the one described with reference to FIGS. 1 and 2. The sleeve 20 is fixed on the optics tube 1 by laser welding with a laser beam 22 via the weld point 23 or a weld seam preferably oriented transversely with respect to the longitudinal axis of the optics tube.

As is shown in FIG. 3, the aperture stop 21 can be designed as a separate structural part which is inserted into the sleeve 20 before or together with the rod lenses 2, 3. In particular, the aperture stop can likewise be made of a weldable material and can be welded to the sleeve 20 in the welding operation, as is indicated in FIG. 3 by the weld point 23 reaching as far as the aperture stop 21. However, the aperture stop 21 can also be connected to the sleeve 20 by adhesive bonding, for example, or can be designed in one piece with the latter (not shown).

FIG. 2 shows a first method for positioning the rod lenses 2, 3 in the longitudinal direction of the optics tube 1. Here, the sleeve 6 is moved inside the optics tube 1 with the aid of a positioning tube 16 of a gauge 17. The positioning tube 16 has an internal diameter which is greater than the internal diameter of the rod lens 3, such that the latter can be enclosed, and the end face of the positioning tube 16 bears directly on an end face of the sleeve 6. As is indicated symbolically in FIG. 2, the sleeve 6 can be pushed by the gauge 17 until the gauge 17 comes into abutment with a proximal or distal end of the optics tube 1, wherein the positioning tube 16 has a length adapted to the predefined position of the rod lens 3 or of the sleeve 6. It is also conceivable that the gauge 17 with the positioning tube 16 does not come into abutment but is instead inserted to a degree into the optics tube 1 in order to push the rod lens 3 to the predefined position that has been determined in the design of the lens system. A similar procedure is performed for the rod lens 2 and for the other lenses of the optical system. In this way, the predefined air gaps between the lenses are also adjusted. It will be appreciated that this method can also be applied to the embodiment shown in FIG. 3.

Figure 4:
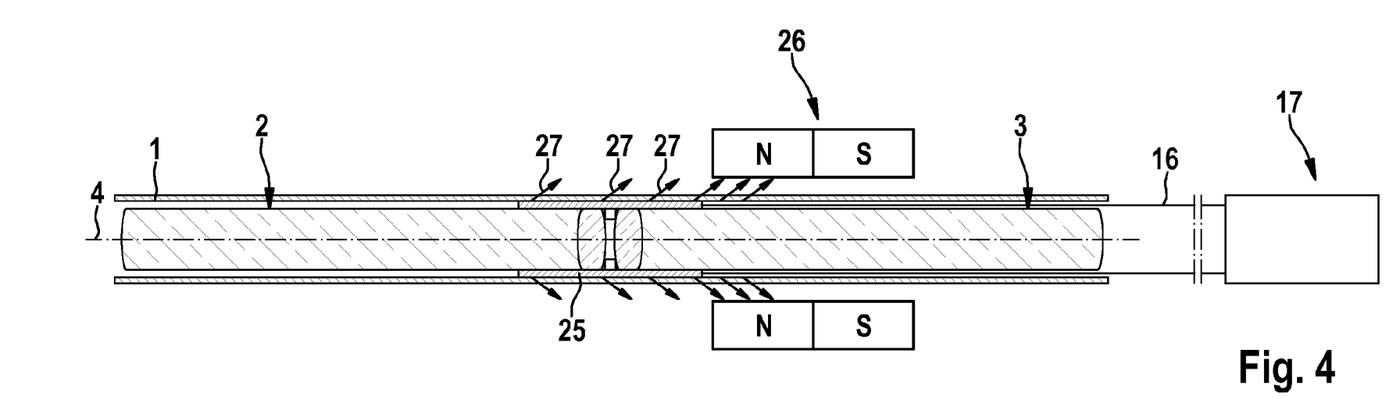
FIG. 4 shows the portion of the optics tube according to FIG. 3, and also an assembly step of a second method according to the invention for mounting the rod lenses in the inside of the optics tube.

Whereas in the above-described longitudinal positioning step, each sleeve 5, 6, 20 is held simply by friction upon contact with the end face of the positioning tube 16, the bearing of the sleeve on the positioning tube 16, and therefore the positioning accuracy, can be improved by the method shown in FIG. 4. In this case, the sleeve 25 is made from a ferromagnetic material and is drawn to the end face of the positioning tube 16 by a coaxially arranged external magnet 26, which is held offset toward the gauge 17 in relation to the sleeve 25. The force thereby generated is indicated symbolically by the arrows 27. In particular, the sleeve can be made from a magnetically soft ferromagnetic material, such that any arrangement of the poles of the magnet 26 indicated by way of example in FIG. 4 is suitable for generating a corresponding pulling force. As has been explained above, the positioning tube 16 is pushed into the optics tube 1 to a certain degree or until abutment, such that the sleeve 25 and the rod lenses 2, 3 reach their predefined position in the longitudinal direction of the optics tube 1.

Figure 5:
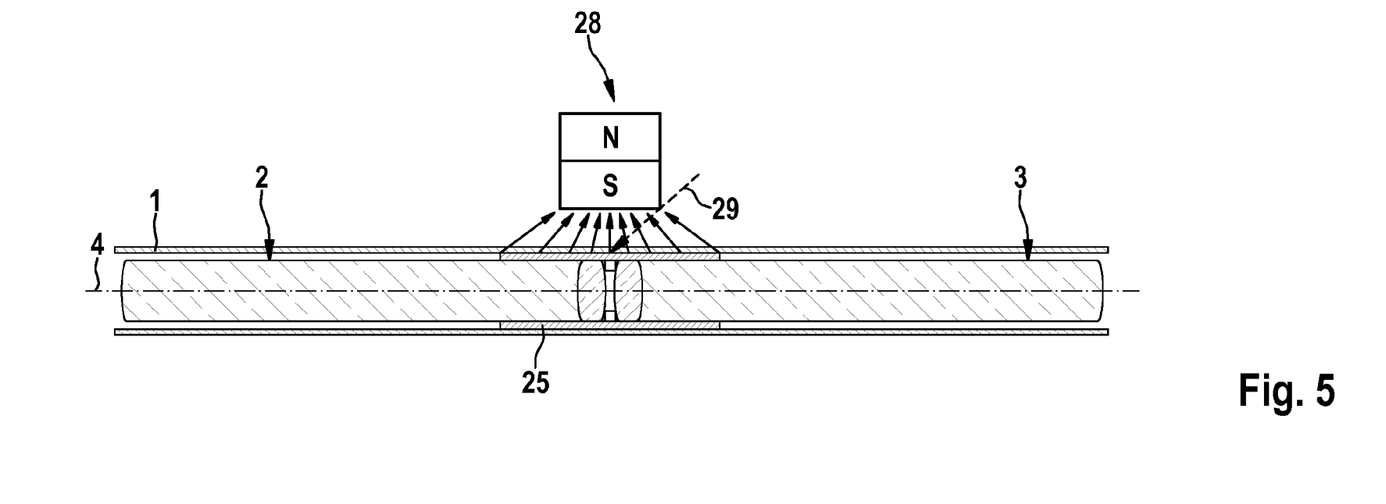
FIG. 5 shows the illustrative embodiment according to FIGS. 3 and 4 in a further step of the second assembly method.

As is shown in FIG. 5, the magnetic sleeve 25 can be pressed in one direction onto the inside face of the optics tube 1 by a magnet 28 arranged laterally of the optics tube 1. In this way, a linear contact between the sleeve 25 and the inside face of the optics tube 1 is generated, and the rod lenses 2, 3 are kept axially aligned in the attained position inside the optics tube 1. As has been described above, a weld connection is then generated with the aid of a laser beam 29, and the sleeve 25 is connected to the optics tube 1; the magnet 28 can have a corresponding recess for the laser beam 29. Depending on the underdimensioning of the sleeve 25 in relation to the optics tube 1, the optical axis 4 may be offset with respect to the axis of symmetry of the optics tube 1. By suitable guiding of the magnet 28, it is possible to ensure that the rod lenses of all relay lens systems of the endoscope are fixed in such a way that their optical axes are aligned with one another, such that the quality of the optical image is not impaired by the offset. If the underdimensioning of the sleeve 25 in relation to the optics tube 1 is sufficiently slight, it may be possible to dispense with the lateral pressing by the magnet 28.

Otherwise, the embodiment shown in FIGS. 4 and 5 is designed in the manner described with reference to FIG. 3. It will be appreciated that the assembly steps shown in FIGS. 4 and 5 can be carried out in the same way for a sleeve designed according to FIGS. 1 and 2.

Figure 6:
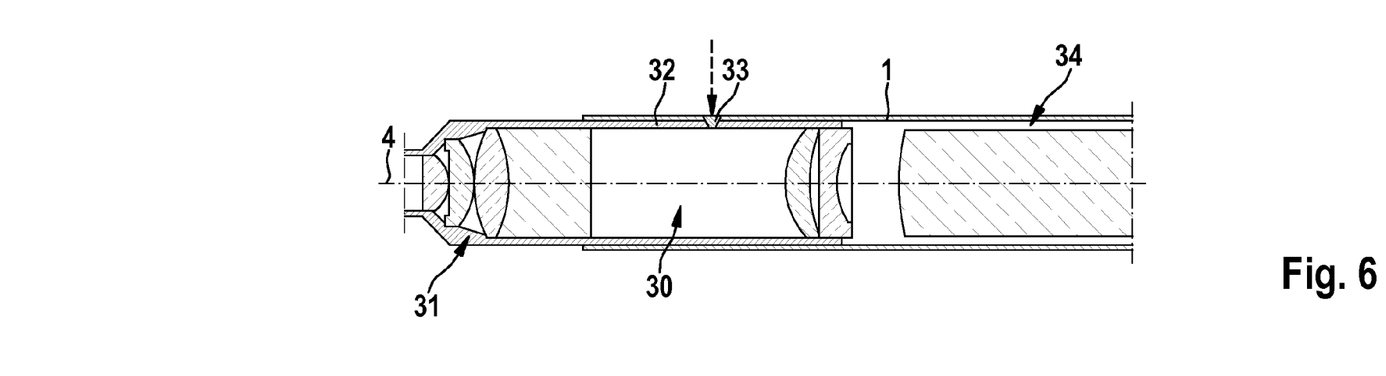
FIG. 6 shows a distal end area of an optics tube with an objective of the endoscope in schematic longitudinal section.
Figure 7:
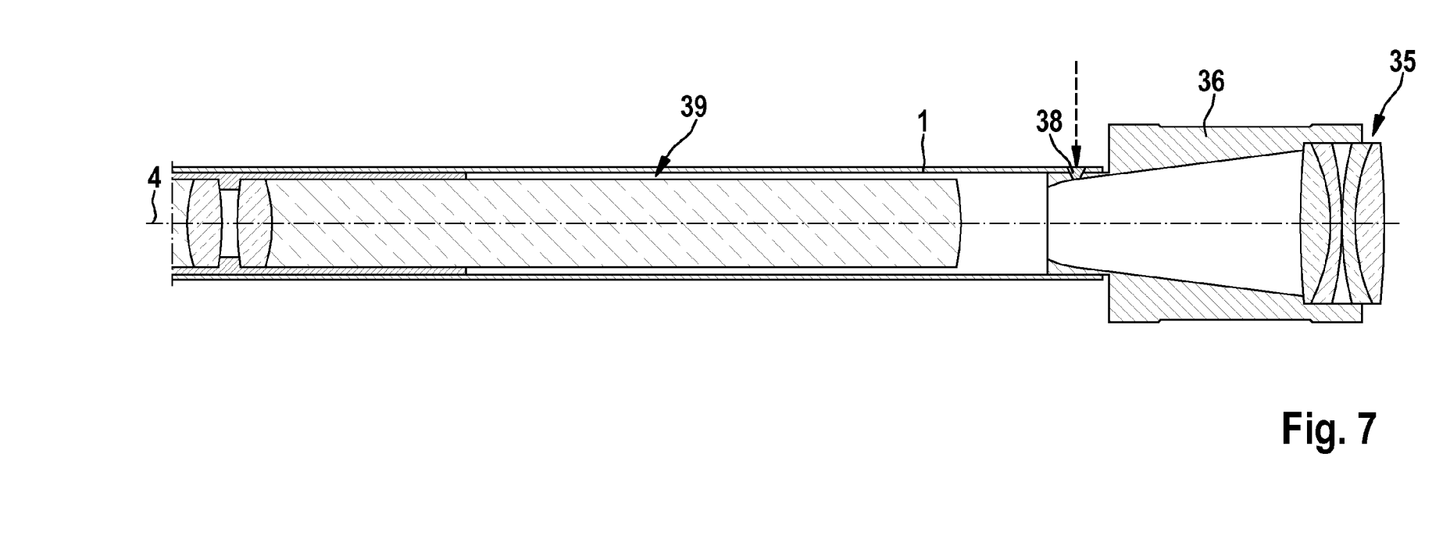
FIG. 7 shows a proximal end area of an optics tube with an eyepiece of the endoscope in schematic longitudinal section.

As is shown by way of example in FIGS. 6 and 7, the objective and/or an eyepiece of the endoscope can also be welded to the optics tube. The objective 30 comprises an objective lens arrangement 31, which is held in an objective sleeve 32. The objective sleeve 32 can be pushed into the optics tube 1 and can be welded thereto. After it has been pushed into a predefined axial position, the objective sleeve 32 is, as has been described above, connected to the optics tube 1 by one or more weld points 33 or by one or more linear weld seams or also by a circular weld seam. According to FIG. 7, an eyepiece has an eyepiece lens arrangement 35, which is arranged in an eyepiece unit 36 which, at the distal end, merges into a cylindrical nozzle 37 that can be pushed into the proximal end of the optics tube 1 and is welded to the latter as has been described above, for example via a weld point 38 or a weld seam. In FIGS. 6 and 7, a distal rod lens 34 and a proximal rod lens 39 are shown inside the optics tube, which rod lenses are designed as has been described above and are fixed inside the optics tube 1.

Figure 8:
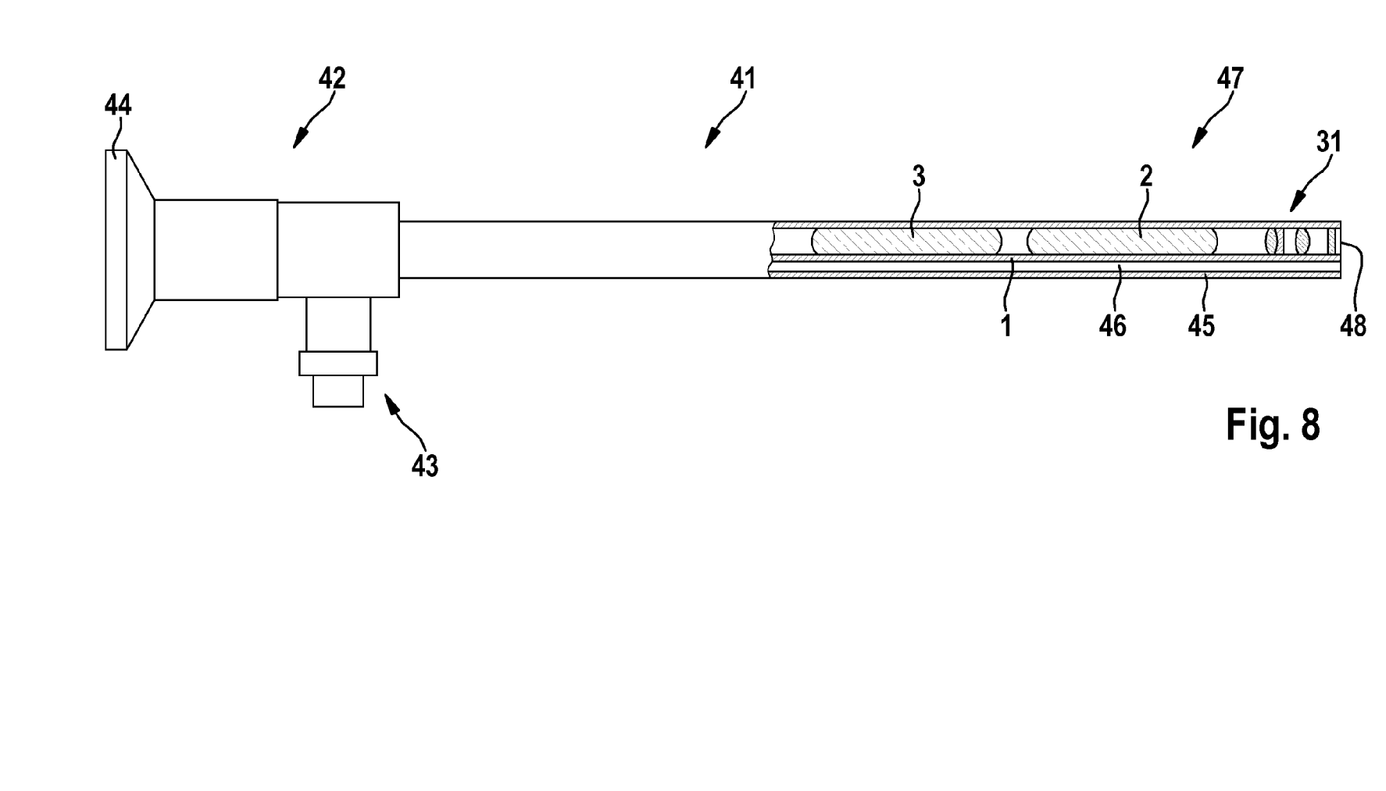
FIG. 8 shows an endoscope in a partially cutaway side view.

FIG. 8 shows a schematic view of an example of an endoscope 40 designed as an endoscope lens system with an optics tube 1 according to the illustrative embodiments described above. The endoscope comprises an elongate endoscope shaft 41, designed to be inserted into an internal cavity of a body, and a head 42 which is arranged at the proximal end of the endoscope shaft 41 and which has a light attachment 43 and an eyepiece with an eyepiece cup 44. The optics tube 1 and light guides 46, through which the illumination light coupled in at the light attachment 43 is transferred to the distal end area 47 of the endoscope 40, are arranged inside the outer tube 45. The interior of the optics tube 1 accommodates objective lens arrangement 31 and also rod lenses 2, 3, by means of which the endoscopic image projected from the objective lens arrangement 31 is transferred from the distal end area 47 to the proximal end area of the endoscope 40 with the eyepiece. At the distal end, the optics tube 1 or endoscope shaft 41 is closed off hermetically by a cover glass 48. The sleeves fixed on the rod lenses 2, 3 and welded to the optics tube 1 are not shown in FIG. 8.

For the sake of clarity, not all reference signs are shown in all of the figures. Reference signs that are not explained in connection with one figure have the same meaning as in the other figures.

The invention claimed is:

1. An endoscope, comprising:
    an optics tube;
    a lens arrangement having a rod lens received in an inside of the optics tube; and
    a sleeve fixed on the rod lens and at least partially enclosing the rod lens;
    wherein at least an axial section of the sleeve that extends circumferentially about the rod lens is welded to the optics tube.

2. The endoscope of claim 1, wherein the optics tube and the sleeve are made of a metallic material.

3. The endoscope of claim 1, wherein the sleeve is adhesively bonded to the rod lens.

4. The endoscope of claim 1, wherein the sleeve encloses the rod lens along a guide length is smaller than a length of the rod lens and which amounts to at most one third of the length of the rod lens.

5. The endoscope of claim 4, wherein the sleeve is fixed centrally on the rod lens.

6. The endoscope of claim 1, wherein the rod lens is a first rod lens and the lens arrangement includes a second rod lens which is adjacent to the first rod lens, and the sleeve encloses mutually facing end portions of the first and second rod lenses and is fixed thereon.

7. The endoscope of claim 6, wherein an annular aperture stop is arranged between the first and second rod lenses.

8. The endoscope of claim 1, wherein the sleeve has a ferromagnetic material.

9. An endoscope, comprising:
    an optics tube including a lens arrangement having a rod lens received in an inside of the optics tube; and
    a sleeve fixed on the rod lens and at least partially enclosing the rod lens;
    wherein at least an axial section of the sleeve that extends circumferentially about the rod lens is welded to the optics tube.

10. A method for mounting a rod lens in an inside of an optics tube, the method comprising:
    fixing a sleeve on the rod lens;
    pushing the rod lens with the sleeve into the optics tube; and
    welding to the optics tube at an axial section of the sleeve that extends circumferentially about the rod lens.

11. The method of claim 10, wherein the sleeve has a ferromagnetic material; and
    wherein the method further comprises positioning the sleeve at a predefined position inside the optics tube under an effect of a magnetic force; and
    welding the sleeve to the optics tube in the predefined position.

12. The method of claim 11, further comprising moving the sleeve in an axial direction with a gauge in order to reach an axial position, in so doing holding the sleeve magnetically against a front face of the gauge; and
    welding the sleeve to the optics tube in the axial position reached.

13. The method of claim 11, further comprising pressing the sleeve in one direction onto an inside face of the optics tube by a laterally acting magnetic force; and
    welding the sleeve to the optics tube in this position.

14. The method of claim 10, further comprising placing the optics tube in a V-shaped groove of an assembly device and, using a laterally acting force, deforming the optics tube in such a way that the sleeve bears at one or more circumferentially distributed contact lines on an inside face of the optics tube; and
    welding the sleeve to the optics tube in an area of at least one of the contact lines.

\* \* \* \* \*